(12) United States Patent
Fu et al.

(10) Patent No.: US 10,456,297 B2
(45) Date of Patent: Oct. 29, 2019

(54) SYSTEMS AND METHODS FOR SYNCHRONIZED THREE-DIMENSIONAL LASER INCISIONS

(71) Applicant: AMO Development, LLC, Santa Ana, CA (US)

(72) Inventors: Hong Fu, Pleasanton, CA (US); Patrick De Guzman, Orange, CA (US); Robert Heitel, Laguna Beach, CA (US); Alireza Malek Tabrizi, Irvine, CA (US)

(73) Assignee: AMO Development, LLC, Santa Ana, CA (US)

( * ) Notice: Subject to any disclaimer, the term of this patent is extended or adjusted under 35 U.S.C. 154(b) by 499 days.

(21) Appl. No.: 14/848,733

(22) Filed: Sep. 9, 2015

(65) Prior Publication Data
US 2016/0067095 A1   Mar. 10, 2016

Related U.S. Application Data

(63) Continuation of application No. 62/048,118, filed on Sep. 9, 2014.

(51) Int. Cl.
*A61F 9/008* (2006.01)

(52) U.S. Cl.
CPC ...... *A61F 9/00836* (2013.01); *A61F 9/00825* (2013.01); *A61F 2009/00844* (2013.01); *A61F 2009/00872* (2013.01); *A61F 2009/00897* (2013.01)

(58) Field of Classification Search
CPC .............. A61F 9/00836; A61F 9/00825; A61F 2009/00844; A61F 2009/00872; A61F 2009/00897

USPC ............................................................. 606/4
See application file for complete search history.

(56) References Cited

U.S. PATENT DOCUMENTS

| 4,665,913 A | 5/1987 | L'Esperance, Jr. |
| 4,669,466 A | 6/1987 | L'Esperance |
| 4,732,148 A | 3/1988 | L'Esperance, Jr. |
| 4,764,930 A | 8/1988 | Bille et al. |

(Continued)

FOREIGN PATENT DOCUMENTS

| DE | 102008017293 A1 | 10/2009 |
| WO | 2005011546 A1 | 2/2005 |
| WO | 2010091419 A1 | 8/2010 |

OTHER PUBLICATIONS

International Search Report and Written Opinion for Application No. PCT/US2015/049121, dated Dec. 7, 2015, 14 pages.

*Primary Examiner* — Michael W Kahelin
*Assistant Examiner* — Vynn V Huh
(74) *Attorney, Agent, or Firm* — Johnson & Johnson Surgical Vision, Inc.

(57) ABSTRACT

Embodiments of this invention generally relate to ophthalmic laser procedures and, more particularly, to systems and methods for creating synchronized three-dimensional laser incisions. In an embodiment, an ophthalmic surgical laser system comprises a laser delivery system for delivering a pulsed laser beam to a target in a subject's eye, an XY-scan device to deflect the pulsed laser beam, a Z-scan device to modify a depth of a focus of the pulsed laser beam, and a controller configured to synchronize an oscillation of the XY-scan device and an oscillation of the Z-device to form an angled three-dimensional laser tissue dissection.

16 Claims, 11 Drawing Sheets

(56) References Cited

U.S. PATENT DOCUMENTS

| | | | |
|---|---|---|---|
| 4,770,172 A | | 9/1988 | L'Esperance, Jr. |
| 4,773,414 A | | 9/1988 | L'Esperance, Jr. |
| 5,108,388 A | | 4/1992 | Trokel et al. |
| 5,163,934 A | | 11/1992 | Munnerlyn |
| 5,207,668 A | | 5/1993 | L'Esperance, Jr. |
| 5,219,343 A | | 6/1993 | L'Esperance, Jr. |
| 5,646,791 A | | 7/1997 | Glockler |
| 5,993,438 A | | 11/1999 | Juhasz et al. |
| 6,315,413 B1 | | 11/2001 | Shimmick et al. |
| RE37,504 E | * | 1/2002 | Lin .................. A61F 9/008 606/5 |
| 6,887,231 B2 | * | 5/2005 | Mrochen ............ A61F 9/00806 606/10 |
| 8,394,084 B2 | | 3/2013 | Blumenkranz et al. |
| 8,403,921 B2 | | 3/2013 | Blumenkranz et al. |
| 8,690,862 B2 | | 4/2014 | Palanker et al. |
| 8,709,001 B2 | | 4/2014 | Blumenkranz et al. |
| 2007/0219543 A1 | * | 9/2007 | Yee .................... A61F 9/00829 606/5 |
| 2011/0172649 A1 | | 7/2011 | Schuele et al. |
| 2013/0144277 A1 | | 6/2013 | Rathjen et al. |
| 2013/0338648 A1 | * | 12/2013 | Hanebuchi ............. A61F 9/008 606/4 |
| 2014/0104576 A1 | | 4/2014 | Bor et al. |
| 2014/0257259 A1 | * | 9/2014 | Papastathopoulos ....................... A61F 9/00825 606/4 |

* cited by examiner

SYSTEMS AND METHODS FOR SYNCHRONIZED THREE-DIMENSIONAL LASER INCISIONS

This application is a non-provisional application and claims the benefit under 35 U.S.C. § 119(e) of U.S. Provisional Patent Application No. 62/048,118, filed Sep. 9, 2014, the full disclosures of all of which are incorporated herein by reference.

FIELD OF THE INVENTION

Embodiments of this invention generally relate to laser-assisted ophthalmic procedures, and more particularly, to systems and methods for synchronized three-dimensional laser incisions.

BACKGROUND

Eye surgery is now commonplace with some patients pursuing it as an elective procedure to avoid using contact lenses or glasses to correct myopia, hyperopia, and astigmatism, and others pursuing it to correct adverse conditions such as cataracts. Moreover, with recent developments in laser technology, laser surgery is becoming the technique of choice for ophthalmic procedures. Indeed, some surgeons prefer a surgical laser beam over manual tools like microkeratomes and forceps, because the laser beam can be focused precisely on extremely small amounts of ocular tissue, thereby enhancing accuracy and reliability of the procedure.

Typically, different laser eye surgical systems use different types of laser beams for the various procedures and indications. These include, for instance, ultraviolet lasers, infrared lasers, and near-infrared, ultra-short pulsed lasers.

For example, in the commonly-known LASIK (Laser Assisted In Situ Keratomileusis) procedure, an ultra-short pulsed laser is used to cut a corneal flap to expose the corneal stroma for photoablation with ultraviolet beams from an excimer laser. Ultra-short pulsed lasers emit radiation with pulse durations as short as 10 femtoseconds and as long as 3 nanoseconds, and a wavelength between 300 nm and 3000 nm.

Besides cutting corneal flaps, surgeons use ultra-short pulsed lasers to perform cataract-related procedures, including creating cataract entry incisions, capsulotomies, as well as fragmenting and softening the cataractous lens prior to enable easier removal. They also use them to create relaxing incisions in the cornea to correct a patient's astigmatism. Examples of laser systems that provide ultra-short pulsed laser beams include the Abbott Medical Optics iFS Advanced Femtosecond Laser, the IntraLase FS Laser, and the Catalys Precision Laser System.

The ability to produce an angled side cut is a highly desired feature in ultra-short pulsed surgical systems used for cutting corneal flaps. This is because the angled side cut enables proper repositioning of the corneal flap after the corneal bed has been ablated with the excimer laser's ultraviolet beams. Proper repositioning of the flap in turn improves the flap edge's regrowth and healing.

Known methods for creating an angled side cut, such as those used in the Abbott Medical Optics iFS system and other conventional ultra-short pulsed laser systems, involve X-Y galvanometers (or "galvos") scanning the laser focus to produce a series of rings of different diameters while the Z-scanner of the system moves slowly vertically. While these methods are suitable for lasers with pulse repetition rates (commonly referred to as "rep-rate") in the hundred KHz range and beam delivery optics covering the entire field of view for corneal flap cutting, they are not optimum for other ophthalmic surgical laser designs that do not meet these characteristics.

Hence, improved systems and methods are needed for making an angled side cut for corneal flap creation during laser ophthalmic surgery.

SUMMARY OF THE INVENTION

Accordingly, this disclosure provides systems and methods for synchronized three-dimensional laser incisions for use in suitable ophthalmic laser surgery systems so as to obviate one or more problems due to limitations and disadvantages of the related art. In one embodiment, an ophthalmic surgical laser system includes a laser delivery system for delivering a pulsed laser beam to a target in a subject's eye, an XY-scan device to deflect the pulsed laser beam, a Z-scan device to modify a depth of a focus of the pulsed laser beam, and a controller configured to synchronize an oscillation of the XY-scan device and an oscillation of the Z-device to form an angled three-dimensional laser tissue dissection. The ophthalmic surgical laser system can form angled three-dimensional laser tissue dissection in any shape using mathematical relation to synchronize the oscillation of the XY-scan device and the oscillation of the Z-device. The ophthalmic surgical laser system is configured to also perform error management and maintain the synchronization of the oscillation of the XY-scan device and the oscillation of the Z-device throughout the procedure. In another embodiment, the ophthalmic surgical laser system also removes tissue during the same procedure. In yet another embodiment, the surgical laser system can be used for non-ophthalmic procedures. In a further embodiment, the laser system can be used for processing non-organic materials, such as for micromachining.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF THE PREFERRED EMBODIMENTS

Embodiments of this invention are generally directed to systems and methods for laser-assisted ophthalmic procedures, and more particularly, to systems and methods for synchronized three-dimensional laser incisions. In one embodiment, the system has a femtosecond oscillator-based laser operating at a repetition rate in the MHz range, for example, 10 MHz or higher, and produces an angled side cut for cutting a corneal flap.

Figure 1:
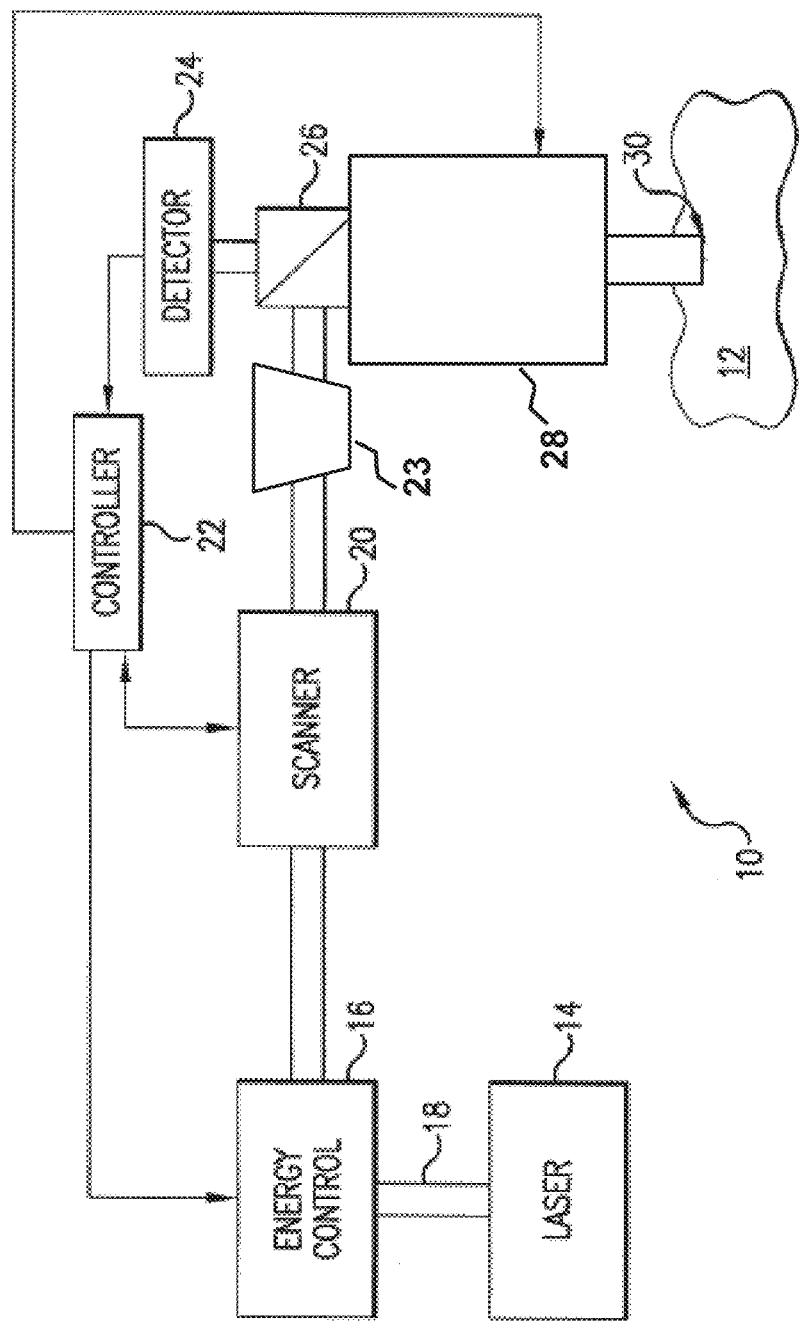
FIG. 1 is a perspective view of a surgical ophthalmic laser system according to an embodiment of the present invention.

Referring to the drawings, FIG. 1 shows a system 10 for making an incision in a material 12. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor operating suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20 or the like. In one embodiment, the pattern of pulses may be summarized in machine-readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting in response to the feedback, and may also modify the planned sculpting based at least in part on the feedback. Measurement systems are further described in U.S. Pat. No. 6,315,413, the entire disclosure of which is incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown),— whether one lens or several lenses—, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of material, create a pocket within the material, form removable structures of the material, and the like. The term "scan" or "scanning" refers to the movement of the focal point of the pulsed laser beam along a desired path or in a desired pattern.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam 18 toward the eye. The laser system 10 is capable of generating the pulsed laser beam 18 with physical characteristics similar to those of the laser beams generated by the laser systems disclosed in U.S. Pat. Nos. 4,764,930, 5,993,438, and U.S. patent application Ser. No. 12/987,069, filed Jan. 7, 2011, the entire disclosures of which are incorporated herein by reference.

Figure 2:
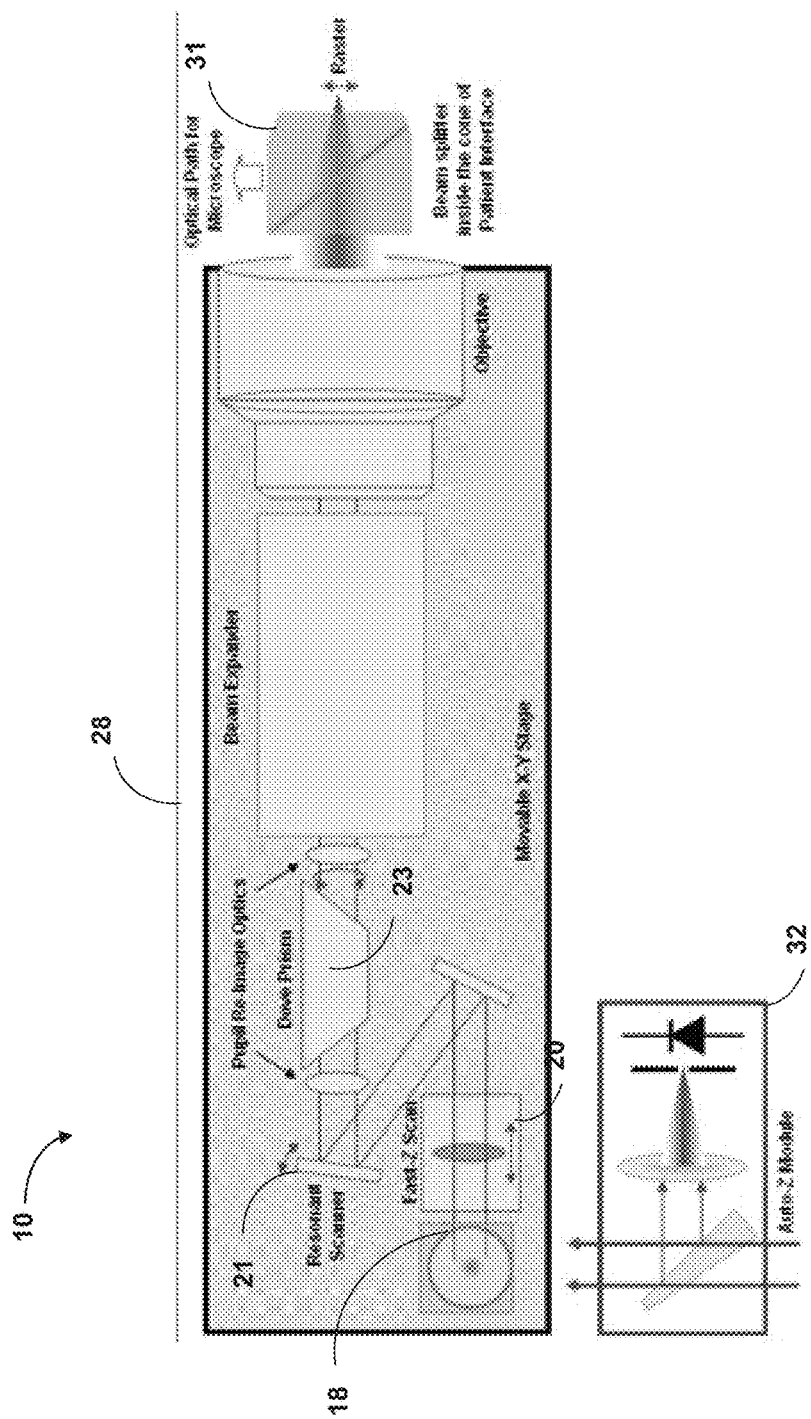
FIG. 2 is another perspective view of a surgical ophthalmic laser system according to an embodiment of the present invention.

FIG. 2 shows another exemplary diagram of the system 10. FIG. 2 shows a moveable XY-scanner (or XY-stage) 28 of a miniaturized femtosecond laser system. In this embodiment, the system 10 uses a femtosecond oscillator or a fiber oscillator-based low energy laser. This allows the laser to be made much smaller. The laser-tissue interaction is in the low-density-plasma mode. An exemplary set of laser parameters for such lasers include pulse energy in the 50-100 nJ range and pulse repetitive rates (or "rep rates") in the 5-20 MHz range. A fast-Z scanner 20 and a resonant scanner 21 direct the laser beam 18 to the prism 23. When used in an ophthalmic procedure, the system 10 also includes a patient interface 31 design that has a fixed cone nose and a portion that engages with the patient's eye. A beam splitter is placed inside the cone of the patient interface to allow the whole eye to be imaged via visualization optics. In one embodiment, the system 10 uses: optics with a 0.6 numerical aperture (NA) which would produce 1.1 μm Full Width at Half Maximum (FWHM) focus spot size; and a resonant scanner 21 that produces 1-2 mm scan line with the XY-scanner scanning the resonant scan line to a 10 mm field.

The prism 23 rotates the resonant scan line in any direction on the XY plane. The fast-Z scanner 20 sets the incision depth and produces a side cut. The system 10 may also include an auto-Z module 32 to provide depth reference. It should be noted that the miniaturized femtosecond laser system 10 may be a desktop system to allow treatment of the patient sitting in an upright position. This eliminates the need of certain optomechanic arm mechanisms, and greatly reduces the complexity, size, and weight of the laser system. Alternatively, the miniaturized laser system may be designed as a conventional femtosecond laser system, where the patient is treated while lying down.

Figure 3:
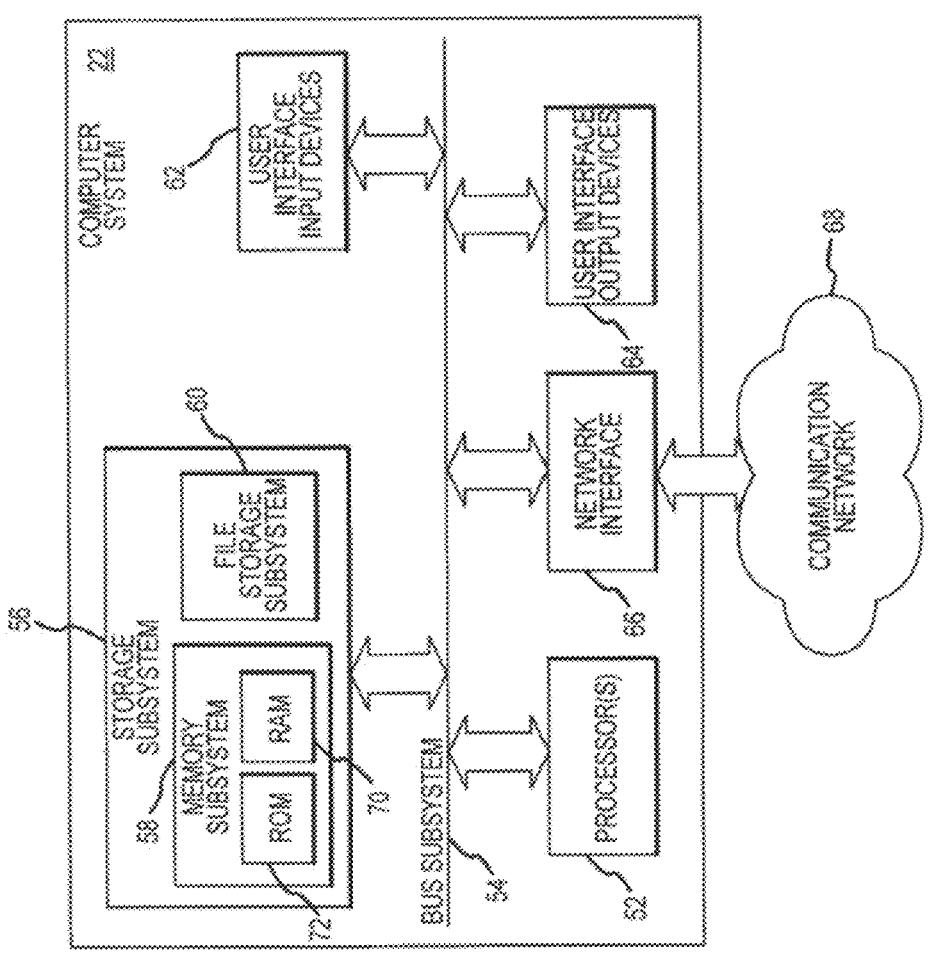
FIG. 3 is a simplified diagram of a controller of a surgical ophthalmic laser system according to an embodiment of the present invention.

FIG. 3 illustrates a simplified block diagram of an exemplary controller 22 that may be used by the laser surgical system 10 according to an embodiment of this invention. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 3 is intended only as an example for purposes of illustrating one embodiment of the present invention. Many other configurations of controller 22, having more or fewer components than those depicted in FIG. 3, are possible.

As should be understood by those of skill in the art, additional components and subsystems may be included with laser system 10. For example, spatial and/or temporal integrators may be included to control the distribution of energy within the laser beam, as described in U.S. Pat. No. 5,646,791, which is incorporated herein by reference. Ablation effluent evacuators/filters, aspirators, and other ancillary components of the surgical laser system are known in the art, and may be included in the system. In addition, an imaging device or system may be used to guide the laser beam. Further details of suitable components of subsystems that can be incorporated into an ophthalmic laser system for performing the procedures described here can be found in commonly-assigned U.S. Pat. Nos. 4,665,913, 4,669,466, 4,732,148, 4,770,172, 4,773,414, 5,207,668, 5,108,388, 5,219,343, 5,646,791, 5,163,934, 8,394,084, 8,403,921, 8,690,862, 8,709,001, U.S. application Ser. No. 12/987,069, filed Jan. 7, 2011, and U.S. application Ser. No. 13/798,457 filed Mar. 13, 2013, which are incorporated herein by reference.

In an embodiment, the laser surgery system 10 includes a femtosecond oscillator-based laser operating in the MHz range, for example, 10 MHz, to perform three-dimensional tissue dissection, e.g., corneal flap cutting, during an ophthalmic procedure. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line.

Figure 4:
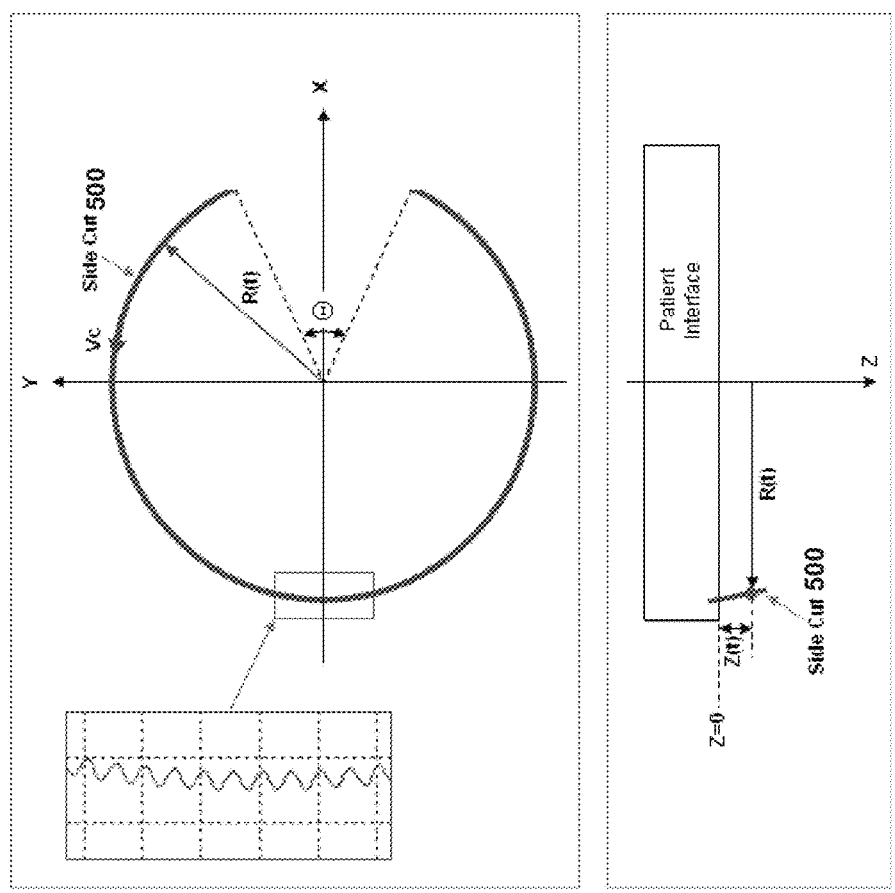
FIG. 4 illustrates a synchronization of an XY-scanner and a Z-scanner of a surgical ophthalmic laser system according to an embodiment of the present invention.

The laser surgery system 10 derives mathematic relations to perform angled side cut (e.g., for a corneal flap cut), and other shaped side cuts that can be realized by synchronizing the motions of the XY-scanner 28 with the motion of the Z-scanner (e.g., fast-Z scanner) 20. In an embodiment, the controller 22 of the laser surgery system 10 synchronizes an oscillation of the XY-scanner 28 and an oscillation of the Z-scanner 20. FIG. 4 illustrates a synchronization of the XY-scanner 28 and the Z-scanner 20. While moving the XY-scanner 28 to perform a (e.g., circular) side cut 500, the radius of the circle is modulated in synchronization with the Z-scanner 20, so that various angled or shaped side cut cross-sections can be obtained. The radius of a side cut as drawn by the XY-scanner 28 at time t, R(t), keeps a fixed relation with side cut depth Z(t), i.e., R=R(Z), where the function can take any form that can form a dissection surface of revolution around the Z-axis passing through the center of the flap. This means that R is a function of Z, i.e., for a given Z, there is only one value of R. Two exemplary functions are:

$$R = R_0 + a \cdot Z, \quad \text{equation (1)},$$

for a linear side cut, and $$R = R_0 + a \cdot Z^2, \quad \text{equation (2)},$$

for a parabolic side cut.

Figure 5B:
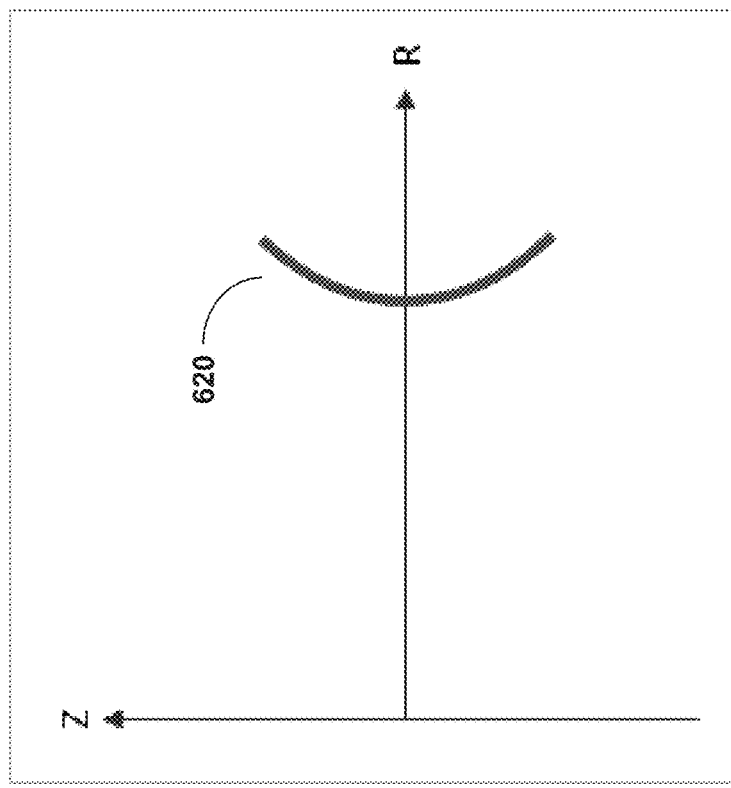
FIGS. 5A and 5B show exemplary cross-sections of side cuts of a surgical ophthalmic laser system according to an embodiment of the present invention.
Figure 5A:
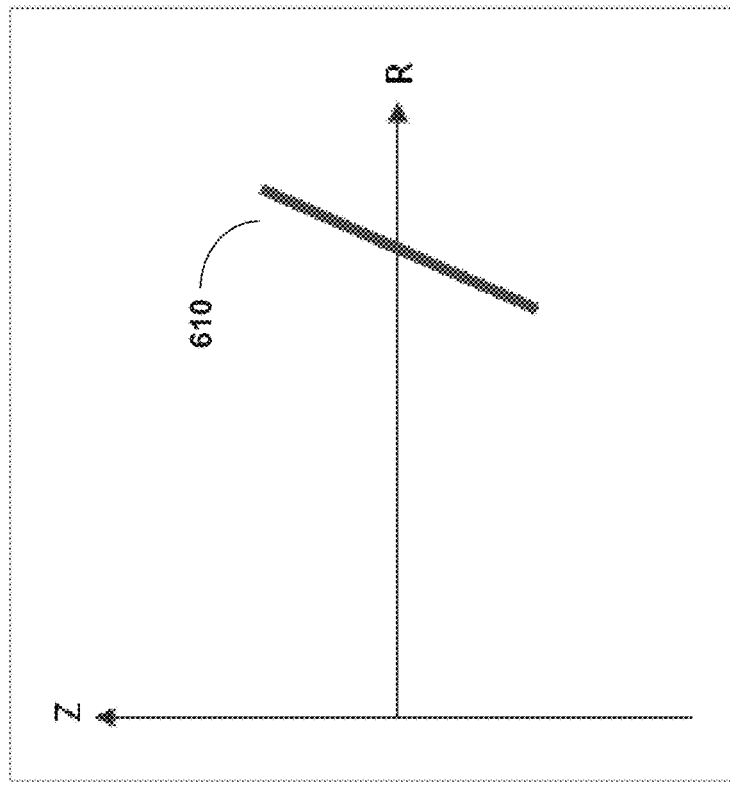

FIGS. 5A and 5B show exemplary cross-sections of side cuts, corresponding to equation (1) and equation (2), respectively. When the line 610 (FIG. 5A) or curve 620 (FIG. 5B) is rotated around the Z-axis, a surface of revolution will be formed. This surface will dissect the tissue within the volume of revolution (e.g., for a corneal flap) from region beyond the volume of revolution (e.g., the rest of the cornea). In general, when R(Z) is a function of Z (i.e., for any given Z, there is a unique value of R), a side cut dissection surface can be formed by rotating the curve R(Z) around the Z-axis.

Figure 6B:
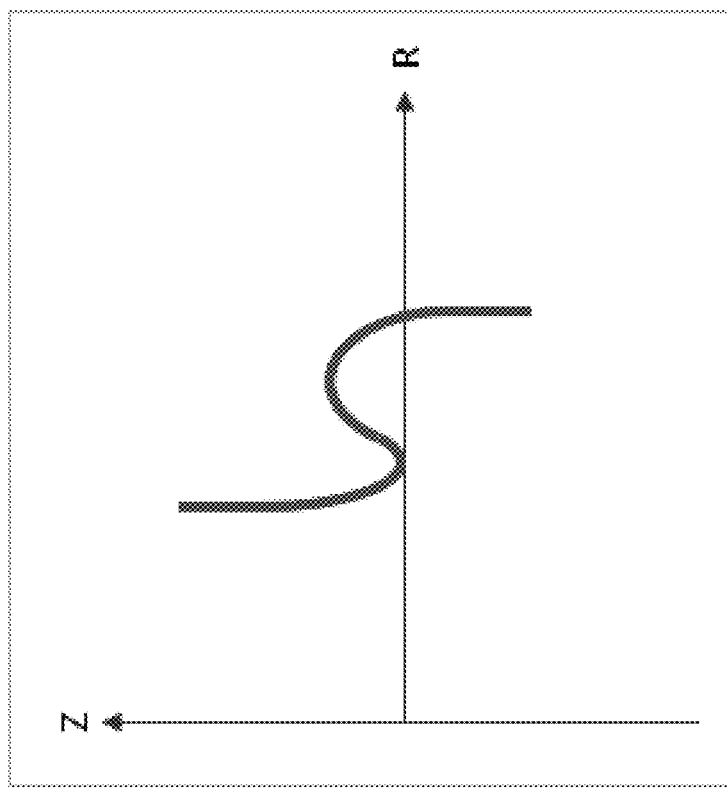
FIGS. 6A and 6B show other exemplary cross-sections of side cuts of a surgical ophthalmic laser system according to an embodiment of the present invention.
Figure 6A:
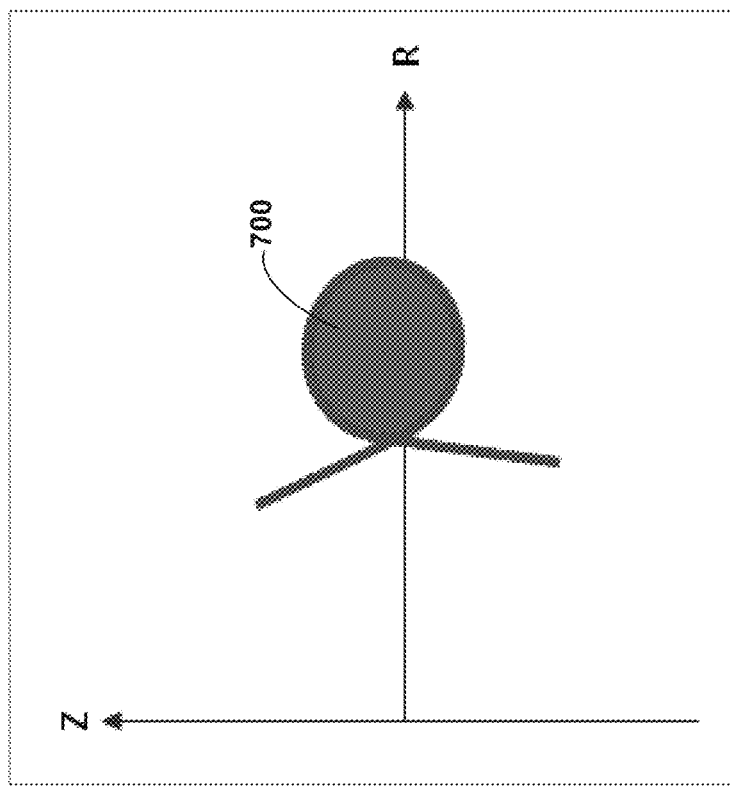

FIGS. 6A and 6B show exemplary cross-sections of side cuts when R(Z) is not a single-valued function of Z. In general, the multi-branched function R(Z) may be categorized into two types. In type 1, as shown in FIG. 6A, R(Z) contains closed loop(s). When the curve R(Z) is rotated around the Z-axis, the side cut will not just dissect but will also remove tissues in the volume marked by the encircled area 700 after revolution around the Z-axis. In type 2, as shown in FIG. 6B, R(Z) is a multi-branched function of Z, but does not contain closed loop. In this case, rotation of the R(Z) curve around the Z-axis will still form a dissection surface without removing material.

In an embodiment, the laser surgery system 10 forms side cut shapes where R(Z) is a single-valued function of Z. In general, for any given function of Z(t), a synchronized side cut can be formed with any given function of R(Z). Using the format of Taylor series, we have $$R(t) = R[Z(t)] = \sum_{n=0}^{\infty} c_n \cdot [Z(t)]^n, \quad \text{equation (3)}$$

where {n} is an integer and {$c_n$} are real number coefficients. Equation (3) is the general format for a synchronized side cut. {n} represents the shape of the cut. For example, when n is 1, the synchronized side cut is linear. The function Z(t) can be any type, depending on the capability of the Z-scanner 20, e.g., a fast-Z scanner. In this embodiment, Z(t) is a sinusoidal function of time, i.e., it only oscillates at a single frequency.

FIGS. 7A to 7D show simulated examples using synchronization relation of:

$$Z(t) = A_Z \cdot \sin(2\pi \cdot f_Z \cdot t), \quad \text{equation (4)}$$

$$X(t) = [R_0 + A_R \cdot \sin(2\pi \cdot f_R \cdot t + \varphi_0)] \cdot \cos\left(\frac{V_C}{R_0} \cdot t + \frac{\Theta}{2}\right), \quad \text{equation (5)}$$

and $$Y(t) = [R_0 + A_R \cdot \sin(2\pi \cdot f_R \cdot t + \varphi_0)] \cdot \sin\left(\frac{V_C}{R_0} \cdot t + \frac{\Theta}{2}\right), \quad \text{equation (6)}$$

where:

X(t) X scanner position as function of time
Y(t) Y scanner position as function of time
Z(t) focus position as function of time
$A_Z$ Amplitude of Z(t) oscillation ($2A_Z$ is equal to the total cutting depth range)
$f_Z$ Fast-Z frequency
$R_0$ Central radius, around which the XY scanner oscillate
$f_R$ Radial oscillation frequency
$A_R$ Amplitude of radial oscillation
$\varphi_0$ Fixed phase difference between Z(t) and R(t)
$\Theta$ Hinge width control parameter expressed in angle.

Figure 7A:
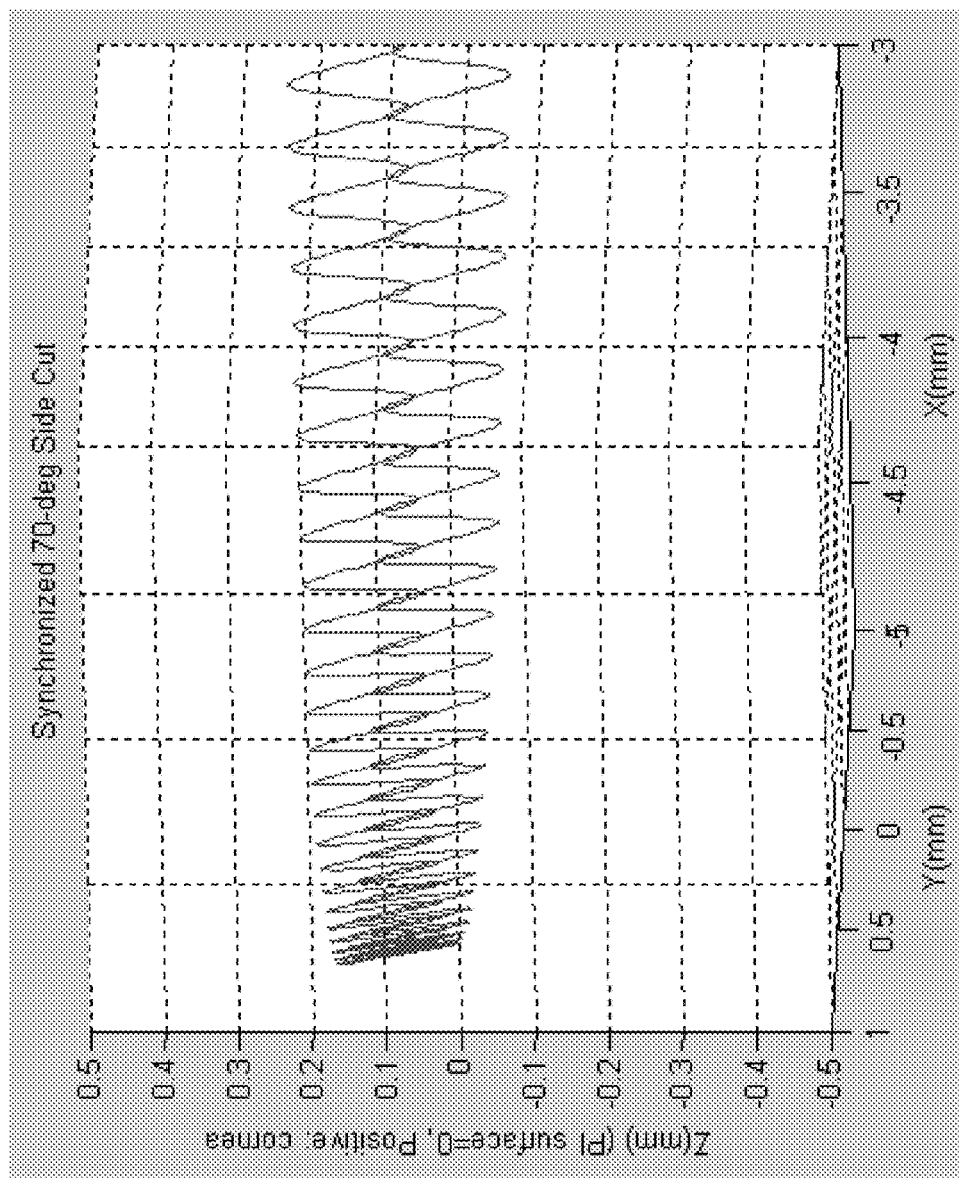
FIGS. 7A to 7D show simulated examples of side cuts of a surgical ophthalmic laser system according to an embodiment of the present invention.
Figure 7B:
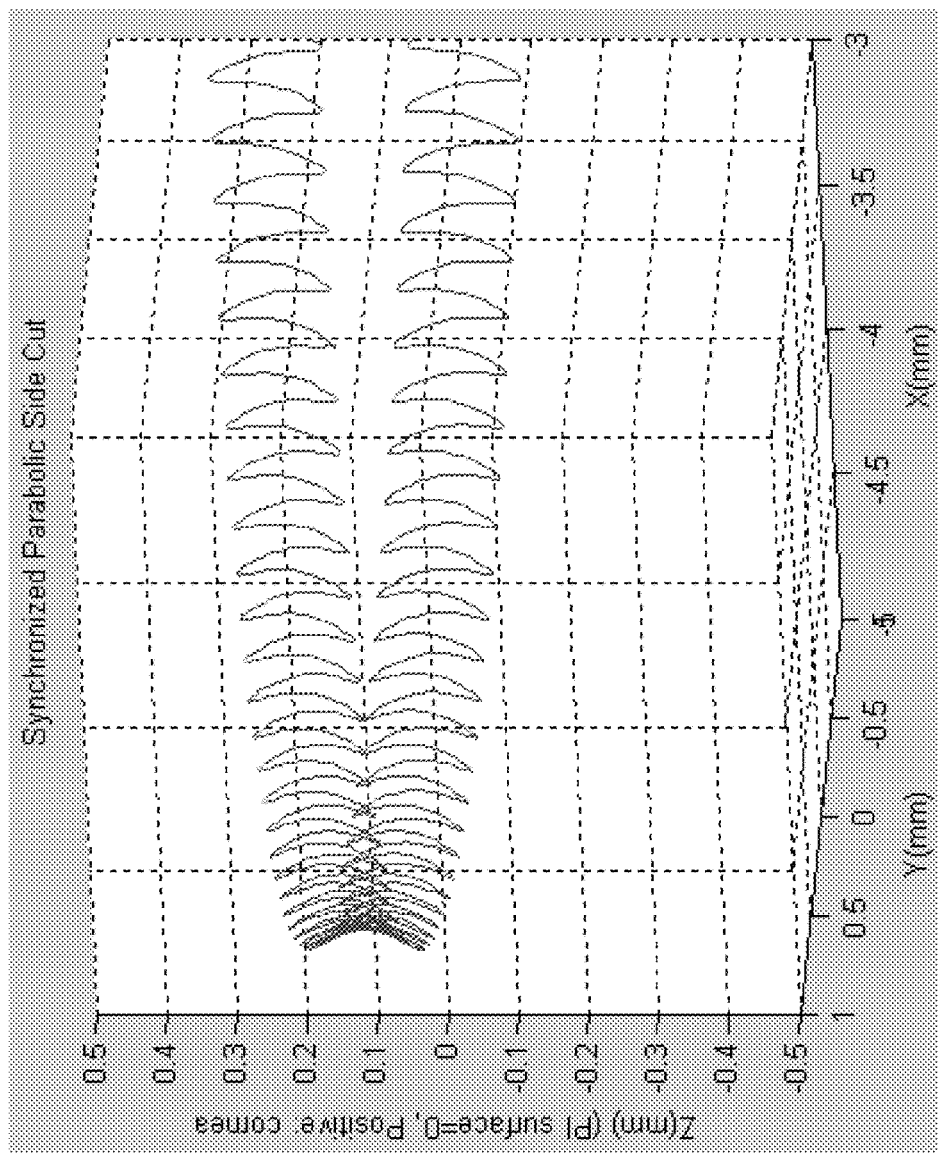
Figure 7C:
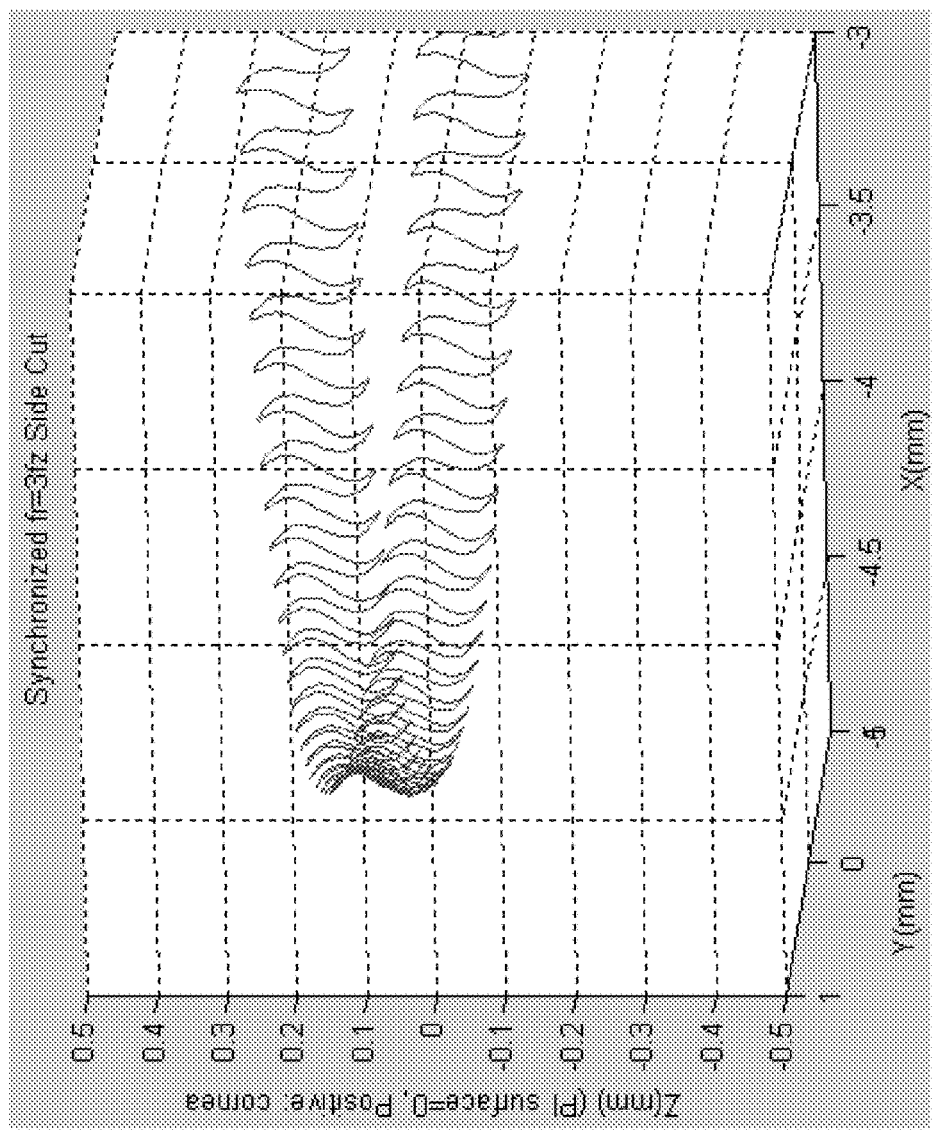
Figure 7D:
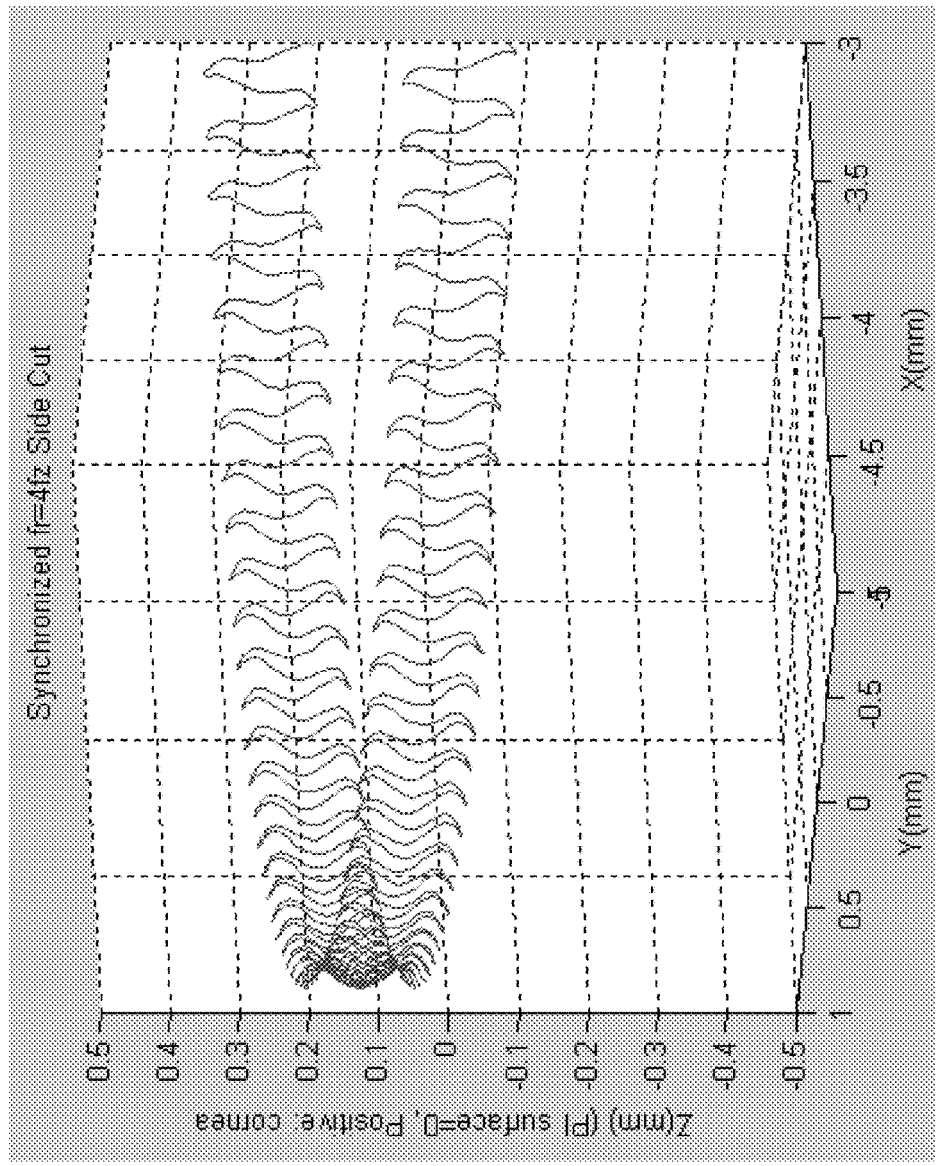

The simulations may be coded using programming language known in the arts, e.g., MATLAB. FIG. 7A shows a 70° side-cut with $A_Z$=80 μm, $f_Z$=20 Hz, $A_R$=$f_R$=20 Hz, $\varphi_0$=0°. FIG. 7B shows a parabolic side-cut with $A_Z$=80 μm, $f_Z$=20 Hz, $A_R$=$f_R$=40 Hz, $\varphi_0$=270°. FIG. 7C shows a $f_R$=$3f_Z$ synchronized side-cut with $A_Z$=80 μm, $f_Z$=20 Hz, $A_R$=$f_R$=60 Hz, $\varphi_0$=180°. FIG. 7D shows a $f_R$=$4f_Z$ synchronized side-cut with $A_Z$=80 μm, $f_Z$=20 Hz, $A_R$=$f_R$=80 Hz, $\varphi_0$=90°.

In an embodiment, the controller 22 maintains the synchronization for the desired initial position and for the fixed relation among the motions of the XY-scanner 28 and the Z-scanner 20 during the entire course of the side cut procedure. In this embodiment, the laser surgery system 10 may establish close-loop feedback among X(t), Y(t), and Z(t) for every cycle of Z(t). In another embodiment, the controller 22 maintains the synchronization for the desired initial position and for the fixed relation among the motions of the XY-scanner 28 and the Z-scanner 20 during the entire course of the side cut procedure without feedback. The laser surgery system 10 also performs error management in order to maintain the synchronization.

In an embodiment, the Z-scanner 20,—e.g., fast-Z-scanner—, can be driven by voice coil mechanism. In another embodiment, the Z-scanning can be realized by using various liquid lens technologies.

It is noted that the synchronized cuts described in the embodiments herein can also be used for laser material processing and micromachining for other transparent materials.

Figure 8:
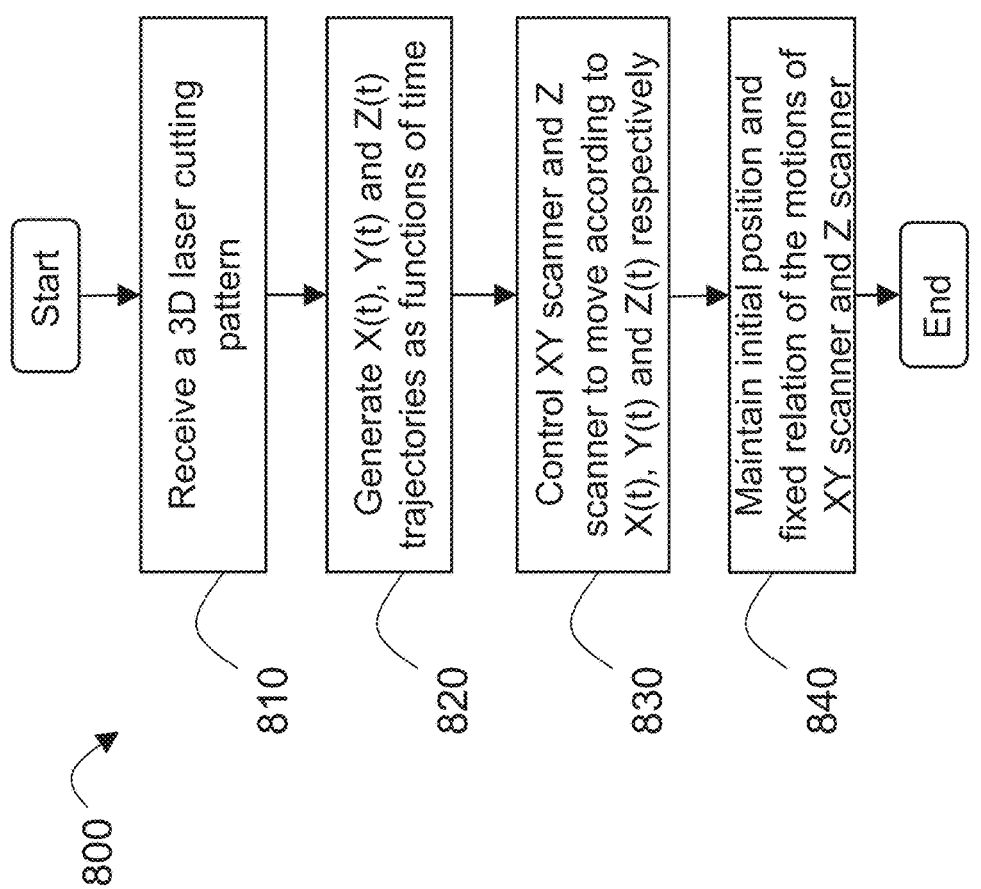
FIG. 8 is a flowchart illustrating a process according to an embodiment of the present invention.

FIG. 8 illustrates a process 800 of the laser surgery system 10 according to an embodiment. The laser surgical system 10 starts the surgical procedure with a predetermined three-dimensional cutting pattern (Action Block 810). The pattern may be received using one or more input devices 62. The pattern may be of any shape as described above. In an ophthalmic surgery procedure, the pattern may be a three dimensional angled tissue dissection without, e.g., an angled side cut of a corneal flap, or with, removal of the tissue. In other non-ophthalmic procedures, the pattern may be a three dimensional angled tissue dissection without, or with, removal of the target material. The laser surgery system 10 generates the X(t), Y(t) and Z(t) trajectories of the XY-scanner 28 and Z-scanner 20, e.g., fast-Z scanner, as function of time (Action Block 820). The trajectories may be generated using an algorithm as shown in Equation (1), (2), or (3) above. The XY-scanner 28 and the Z-scanner 20 are thus synchronized in a fixed relation. The laser surgery system 10 controls the XY-scanner 28 and Z-scanner 20 to move according X(t), Y(t) and Z(t) respectively (Action Block 830). The laser surgery system 10 then maintains the synchronization for the desired initial position and for the fixed relation among the motions of the XY-scanner 28 and the Z-scanner 20 during the entire course of the cut procedure (Action Block 840). To maintain the synchronization, the laser surgery system 10 may establish close-loop feedback among X(t), Y(t), and Z(t) for every cycle of Z(t).

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. An ophthalmic surgical laser system comprising:
   a laser delivery system for delivering a pulsed laser beam to a target in a subject's eye;
   an XY-scan device to deflect the pulsed laser beam;
   a Z-scan device to modify a depth of a focus of the pulsed laser beam along an optical axis; and
   a controller configured to synchronize an oscillation of the XY-scan device and an oscillation of the Z-scan device to form a three-dimensional laser tissue dissection, including to control the XY-scan device to move the focus of the laser beam in a plane perpendicular to the optical axis in an angular direction, which is a direction around the optical axis, from a first angular position to a second angular position once within a time interval while oscillating a radius of the focus, which is a distance from the optical axis, a first plurality of times within the same time interval, and to simultaneously control the Z-scan device to oscillate the depth of the focus a second plurality of times within the same time interval, wherein the first plurality of times is equal to the second plurality of times multiplied by two, three or four.

2. The ophthalmic surgical laser system of claim 1, wherein the synchronization of the XY-scan device and the Z-scan device has a fixed relation over time.

3. The ophthalmic surgical laser system of claim 1, wherein the three-dimensional laser tissue dissection is parabolic and is determined by $R=R_0+a \cdot Z^2$
   where R is a central radius of the XY-scan device, $R_0$ is the central radius of the XY-scan device at time 0, a is a constant, and Z is a focus position of the Z-scan device.

4. The ophthalmic surgical laser system of claim 1, wherein the three-dimensional laser tissue dissection is a shape determined by $$R(t) = R[Z(t)] = \sum_{n=0}^{\infty} c_n \cdot [Z(t)]^n$$

where R(t) is a central radius of the XY-scan device at time t, is Z(t) is a focus position of the Z-scan device at time t, c is a real number coefficient, and n is an integer.

5. The ophthalmic surgical laser system of claim 1, wherein the controller is further configured to perform error management and to maintain the synchronization of the oscillation of the XY-scan device and the oscillation of the Z-scan device.

6. The ophthalmic surgical laser system of claim 1, wherein the controller is furthered configured to remove tissue.

7. The ophthalmic surgical laser system of claim 1, wherein the radius has a predefined relation with the depth.

8. The ophthalmic surgical laser system of claim 1, wherein the controller controls the XY-scan device and the Z-scan device to move the focus according to:

$$Z(t) = A_Z \cdot \sin(2\pi \cdot f_Z \cdot t),$$

$$X(t) = [R_0 + A_R \cdot \sin(2\pi \cdot f_R \cdot t + \varphi_0)] \cdot \cos\left(\frac{V_C}{R_0} \cdot t + \frac{\Theta}{2}\right),$$

and $$Y(t) = [R_0 + A_R \cdot \sin(2\pi \cdot f_R \cdot t + \varphi_0)] \cdot \sin\left(\frac{V_C}{R_0} \cdot t + \frac{\Theta}{2}\right),$$

wherein X(t) is an X position of the focus as a function of time, Y(t) is a Y position of the focus as a function of time, Z(t) is the depth of the focus as a function of time, $f_Z$ is a frequency of oscillation of the depth and $f_R$ is a frequency of oscillation of the X and Y positions, and $A_Z$, $R_0$, $A_R$, $\varphi_0$, and $\Theta$ are control parameters, and wherein $f_R$ equals two times $f_Z$, or three times $f_Z$, or four times $f_Z$.

9. A method for dissecting tissue of an eye using an ophthalmic surgical laser system, the method comprising:
   generating a pulsed laser beam;
   delivering the pulsed laser beam to a target in a subject's eye;
   deflecting, by an XY-scan device, the pulsed laser beam;
   modifying, by a Z-scan device, a depth of a focus of the pulsed laser beam along an optical axis; and synchronizing, by a controller, an oscillation of the XY-scan device with an oscillation of the Z-scan device to form a three-dimensional laser tissue dissection, including controlling the XY-scan device to move the focus of the laser beam in a plane perpendicular to the optical axis in an angular direction, which is a direction around the optical axis, from a first angular position to a second angular position once within a time interval while oscillating a radius of the focus, which is a distance from the optical axis, a first plurality of times within the same time interval, and simultaneously controlling the Z-scan device to oscillate the depth of the focus a second plurality of times within the same time interval, wherein the first plurality of times is equal to the second plurality of times multiplied by two, three or four.

10. The method of claim 9 wherein the synchronization of the XY-scan device with the Z-scan device has a fixed relation over time.

11. The method of claim 9 wherein the three-dimensional laser tissue dissection is parabolic and is determined by $R=R_0+a \cdot Z^2$
where R is a central radius of the XY-scan device, $R_0$ is the central radius of the XY-scan device at time 0, a is a constant, and Z is a focus position of the Z-scan device.

12. The method of claim 9 wherein the three-dimensional laser tissue dissection is a shape determined by $$R(t) = R[Z(t)] = \sum_{n=0}^{\infty} c_n \cdot [Z(t)]^n$$

where R(t) is a central radius of the XY-scan device at time t, is Z(t) is a focus position of the Z-scan device at time t, c is a real number coefficient, and n is an integer.

13. The method of claim 9 wherein the controller is further configured to perform error management to maintain the synchronization of the oscillation of the XY-scan device and the oscillation of the Z-scan device.

14. The method of claim 9, wherein the radius has a predefined relation with the depth.

15. The method of claim 9, wherein the controller controls the XY-scan device and the Z-scan device to move the focus according to:

$$Z(t) = A_Z \cdot \sin(2\pi \cdot f_Z \cdot t),$$

$$X(t) = [R_0 + A_R \cdot \sin(2\pi \cdot f_R \cdot t + \varphi_0)] \cdot \cos\left(\frac{V_C}{R_0} \cdot t + \frac{\Theta}{2}\right),$$

and $$Y(t) = [R_0 + A_R \cdot \sin(2\pi \cdot f_R \cdot t + \varphi_0)] \cdot \sin\left(\frac{V_C}{R_0} \cdot t + \frac{\Theta}{2}\right),$$

wherein X(t) is an X position of the focus as a function of time, Y(t) is a Y position of the focus as a function of time, Z(t) is the depth of the focus as a function of time, $f_Z$ is a frequency of oscillation of the depth and $f_R$ is a frequency of oscillation of the X and Y positions, and $A_Z$, $R_0$, $A_R$, $\varphi_0$, and $\Theta$ are control parameters, and where $f_R$ equals two times $f_Z$, or three times $f_Z$, or four times $f_Z$.

16. An ophthalmic surgical laser system comprising:
a laser delivery system for delivering a pulsed laser beam to a target in a subject's eye;
a resonant scanner;
an XY-scan device to deflect the pulsed laser beam to form one or more scan lines;
a Z-scan device to modify a depth of a focus of the pulsed laser beam along an optical axis; and
a controller configured to synchronize an oscillation of the XY-scan device and an oscillation of the Z-scan device to form a three-dimensional laser tissue dissection into any shape, including to control the XY-scan device to move the focus of the laser beam in a plane perpendicular to the optical axis in an angular direction, which is a direction around the optical axis from a first angular position to a second angular position once within a time interval while oscillating a radius of the focus, which is a distance from the optical axis, a first plurality of times within the same time interval, and to simultaneously control the Z-scan device to oscillate the depth of the focus a second plurality of times within the same time interval, wherein the first plurality of times is equal to the second plurality of times multiplied by two, three or four.

* * * * *